US011446485B2

(12) United States Patent
Swoyer et al.

(10) Patent No.: US 11,446,485 B2
(45) Date of Patent: Sep. 20, 2022

(54) LEAD FOR THE TEMPORARY STIMULATION OF A PERIPHERAL NERVE

(71) Applicant: Nextern, Inc., White Bear Lake, MN (US)

(72) Inventors: John Swoyer, Blaine, MN (US); Jonathan Lawson, Cottage Grove, MN (US); Jesse Geroy, Ham Lake, MN (US)

(73) Assignee: NEXTERN INNOVATION, LLC, White Bear Lake, MN (US)

( * ) Notice: Subject to any disclaimer, the term of this patent is extended or adjusted under 35 U.S.C. 154(b) by 108 days.

(21) Appl. No.: 16/858,452

(22) Filed: Apr. 24, 2020

(65) Prior Publication Data

US 2020/0338340 A1 Oct. 29, 2020

Related U.S. Application Data

(60) Provisional application No. 62/839,357, filed on Apr. 26, 2019.

(51) Int. Cl.
*A61N 1/05* (2006.01)
*A61B 17/34* (2006.01)
(Continued)

(52) U.S. Cl.
CPC ........ *A61N 1/0558* (2013.01); *A61B 17/3468* (2013.01); *A61N 1/3605* (2013.01); *A61N 1/36017* (2013.01); *A61N 1/37518* (2017.08)

(58) Field of Classification Search
CPC .......................................... A61N 1/0553–0558
See application file for complete search history.

(56) References Cited

U.S. PATENT DOCUMENTS 5,366,493 A 11/1994 Scheiner et al.
6,638,237 B1 * 10/2003 Guiles ................. A61F 2/94
604/8
(Continued)

FOREIGN PATENT DOCUMENTS

EP 2914334 B1 8/2019
WO 2009135080 A1 11/2009

OTHER PUBLICATIONS

Jaeho Park, Won-Mook Choi, Kyuyoung Kim, Won-Il Jeong, Joon-Beom Seo, Inkyu Park, Biopsy Needle Integrated with Electrical Impedance Sensing Microelectrode Array towards Real-time Needle Guidance and Tissue Discrimination, Scientific Reports vol. 8, Article No. 264 (2018), retrieved online on Jan. 22, 2020 from <https://www.nature.com/articles/s41598-017-18360-4>, 37 pages, published on Jan. 10, 2018.

(Continued)

*Primary Examiner* — Eric D. Bertram
(74) *Attorney, Agent, or Firm* — Craige Thompson; Thompson Patent Law; Timothy D. Snowden

(57) ABSTRACT

Apparatus and associated methods relate to a lead that includes metallic traces sandwiched between layers of polymers to form a ribbon (e.g., similar to a flex circuit). In an illustrative example, areas on both ends of the traces may be exposed, forming stimulation electrodes on one end and electrical contacts on the other. The ribbon may be formed such that it fits down a small diameter needle. When the needle is removed, the formed ribbon may relax and engage the tissue providing a means of retention. The lead may advantageously: (1) be minimally invasive to implant, (2) be inexpensive, (3) stay in place a temporary/trial medical procedure setting, and (4) be easy to remove.

20 Claims, 8 Drawing Sheets

(51) Int. Cl.
*A61N 1/375* (2006.01)
*A61N 1/36* (2006.01)

(56) References Cited

U.S. PATENT DOCUMENTS

| | | | | |
|---|---|---|---|---|
| 9,486,628 | B2* | 11/2016 | Christopherson | A61N 1/0551 |
| 9,802,038 | B2* | 10/2017 | Lee | A61N 1/36062 |
| 10,207,103 | B2 | 2/2019 | Gonzalez et al. | |
| 10,695,556 | B2* | 6/2020 | Mercanzini | A61B 5/6868 |
| 10,864,374 | B2* | 12/2020 | Hoffer | A61N 1/0551 |
| 2005/0004627 | A1* | 1/2005 | Gibson | A61N 1/0529 |
| | | | | 607/57 |
| 2009/0275996 | A1 | 11/2009 | Burnes et al. | |
| 2009/0275997 | A1* | 11/2009 | Faltys | A61N 1/36053 |
| | | | | 607/2 |
| 2013/0245733 | A1* | 9/2013 | Yomtov | A61N 1/36125 |
| | | | | 607/116 |
| 2014/0296954 | A1 | 10/2014 | Wells | |
| 2017/0340891 | A1 | 11/2017 | Boggs et al. | |

OTHER PUBLICATIONS

Avram Scheiner, G. Polando, E. Byron Marsolais, Design and clinical application of a double helix electrode for functional electrical stimulation, IEEE Transactions, retrieved online on Jan. 22, 2020 from <https://www.semanticscholar.org/paper/Design-and-clinical-application-of-a-double-helix-Scheiner-Polando/07cd0757c2cc4ffca44dd025000df0dbe0480958>, 6 pages, published on 1999.

Janis J Daly, Kathryn Kollar, A. Anna Debogorski, Beth Strasshofer, Byron Marsolais, Avram Scheiner, Scott Snyder, Robert L. Ruff, Performance of an intramuscular electrode during Functional neuromuscular stimulation for gait training post stroke, Journal of Rehabilitation Research & Development, vol. 38 ,retrieved online on Jan. 22, 2020 from <https://www.rehab.research.va.gov/jour/01/38/5/daly.htm>, pp. 513-526, 17 pages, published on 2001.

* cited by examiner

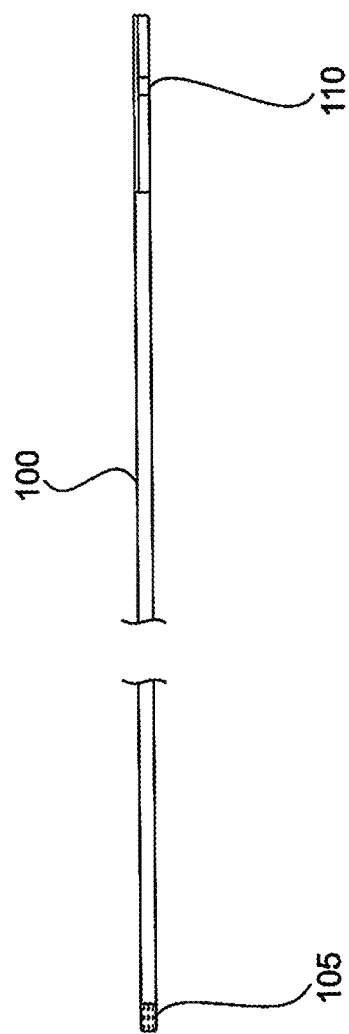

LEAD FOR THE TEMPORARY STIMULATION OF A PERIPHERAL NERVE

CROSS-REFERENCE TO RELATED APPLICATIONS

This application also claims the benefit of U.S. Provisional Application Ser. No. 62/839,357, titled "Lead for the temporary stimulation of a peripheral nerve," filed by John Swoyer, et al., on Apr. 26, 2019.

This application incorporates the entire contents of the foregoing application(s) herein by reference.

TECHNICAL FIELD

Various embodiments relate generally to design of a temporary neurostimulation lead.

BACKGROUND

There are a variety of therapies that involve the stimulation of peripheral nerves for the treatment of disease states. Some of these therapies may be chronic, and others may be acute. For example, sacral nerve stimulation may be an example of chronic stimulation of a nerve for the treatment of overactive bladder and other disorders of the pelvic area. Stimulation of nerves near a joint or muscle may be used for temporary relief of acute pain, while a chronic implant may be used for long-term pain.

SUMMARY

Apparatus and associated methods relate to a lead that includes metallic traces sandwiched between layers of polymers to form a ribbon (e.g., similar to a flex circuit). In an illustrative example, areas on both ends of the traces may be exposed, forming stimulation electrodes on one end and electrical contacts on the other. The ribbon may be formed such that it fits down a small diameter needle. When the needle is removed, the formed ribbon may relax and engage the tissue providing a means of retention. The lead may advantageously: (1) be minimally invasive to implant, (2) be inexpensive, (3) stay in place in a temporary/trial medical procedure setting, and (4) be easy to remove.

Additional uses include stimulation of cranial nerves, included but not limited to the Vagus nerves to treat conditions, including but not limited to, depression or insomnia. The details of various embodiments are set forth in the accompanying drawings and the description below. Other features and advantages will be apparent from the description and drawings, and from the claims.

BRIEF DESCRIPTION OF THE DRAWINGS

FIGS. 1, 1A, 1B, and 1C depict various top perspective views of an exemplary lead ribbon including two traces with exposed ends.

Like reference symbols in the various drawings indicate like elements.

DETAILED DESCRIPTION OF ILLUSTRATIVE EMBODIMENTS

Not all patients respond to stimulation treatments. Therefore, in some situations, it may be desirable to have a trial stimulation to demonstrate efficacy prior to an expensive and invasive procedure to implant a chronic system. To be useful, a temporary/trial procedure may use a lead that is minimally invasive to implant, in a setting such as a doctor's office, be inexpensive, stay in place during the trial, and be easy to remove. Accordingly, disclosed herein is a lead designed to meet the above described requirements.

Figure 1A:
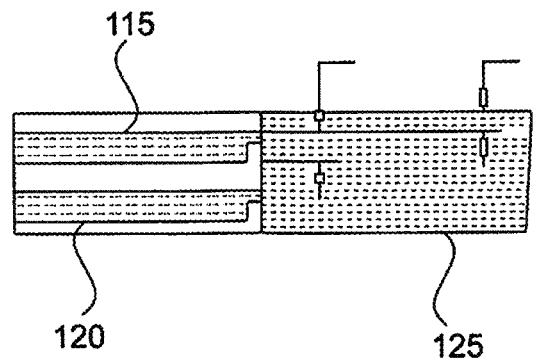
Figure 1B:
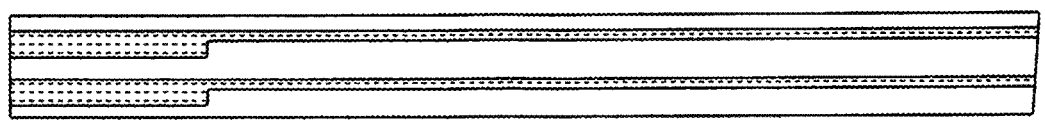

FIGS. 1, 1A, 1B, and 1C depict various top perspective views of an exemplary lead ribbon including two traces with exposed ends. These figures show the lead ribbon 100 (with exemplary dimensions) having two traces 115, 120 with exposed ends. FIG. 1A illustrates finer detail of the proximal end 105 of the straight lead ribbon 100 (detail A shown in FIG. 1), while FIG. 1B illustrates the same detail as FIG. 1A but with the top layer of insulation removed to reveal more of the traces.

Figure 1C:
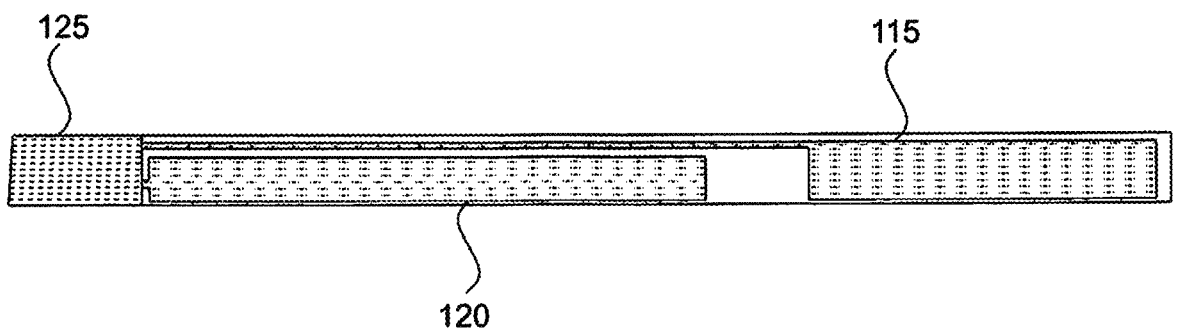

FIG. 1C illustrates finer detail of the distal end 110 of the lead ribbon 100 (detail B shown in FIG. 1). The traces 115, 120 may be covered with insulation 125 (e.g., polyimide), with one side of each end exposed. The distal end 110 may be configured as electrodes (e.g., a pair of pads), with the proximal exposed end 105 used to connect to an electrical stimulator, or a cable that then connects to a stimulator, for example. It is understood that any number, shape or size of traces, electrodes, and connections could be formed in this manner.

Figure 2:
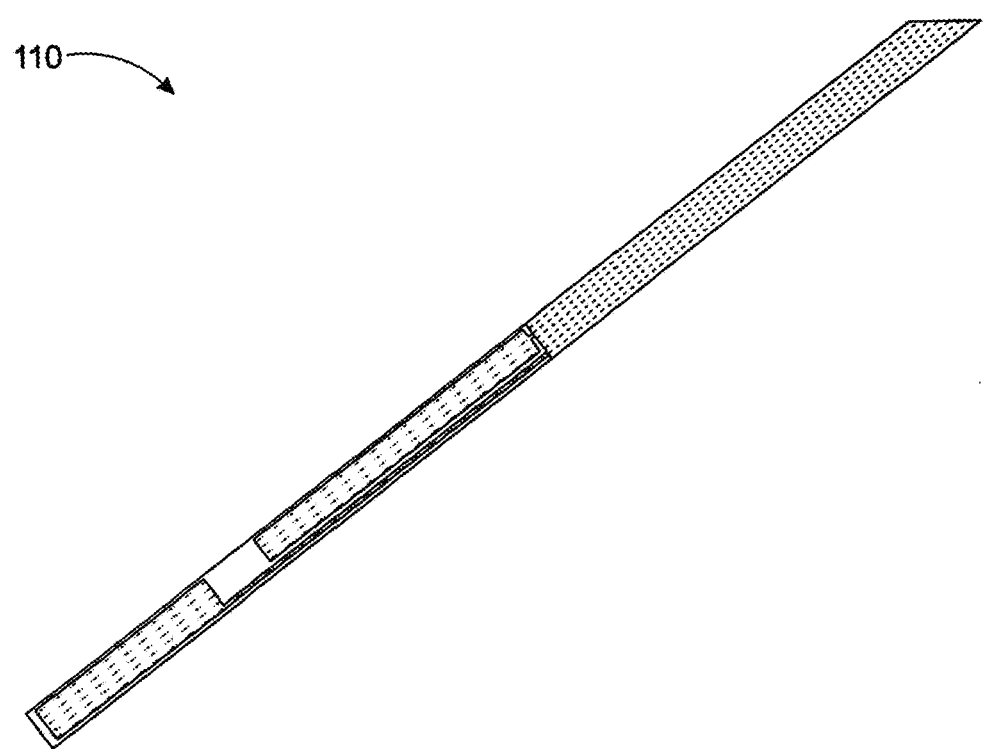
FIG. 2 depicts a perspective view of an exemplary lead, with zoomed in detail on the distal end of the lead illustrating exposed electrodes.

FIG. 2 depicts a perspective view of an exemplary lead, with zoomed in detail on the distal end of the lead illustrating exposed electrodes. This figure shows a close up of the distal end 110, revealing the two exposed electrodes.

Figure 3:
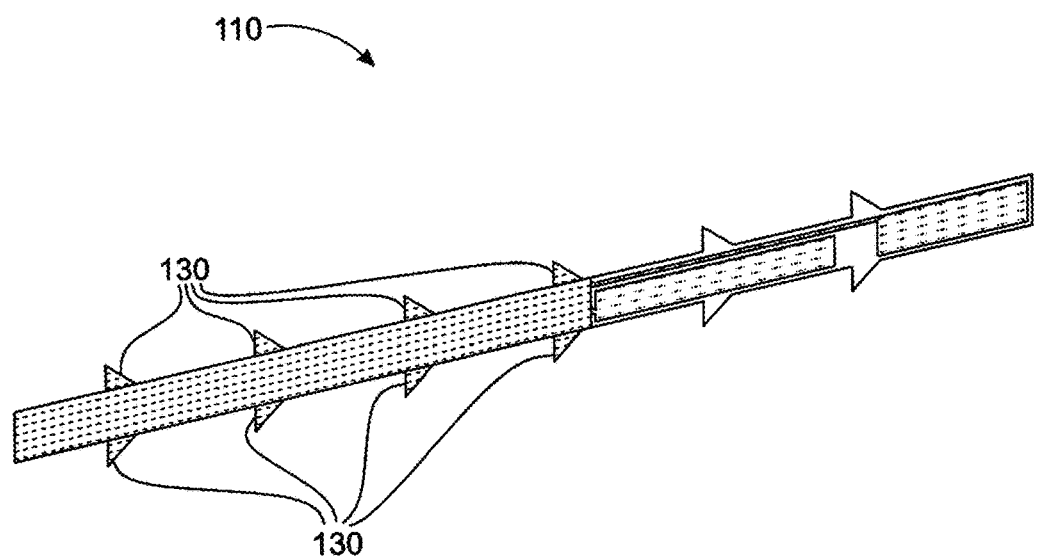
FIG. 3 depicts a perspective view of an exemplary lead, with zoomed in detail on the distal end of the lead illustrating fixation members.

FIG. 3 depicts a perspective view of an exemplary lead, with zoomed in detail on the distal end of the lead illustrating fixation members. In some embodiments, the distal end 110 with optional fixation features/members 130. The fixation members 130 may be formed as multiple teeth, each having a triangular profile, for example. The members 130 may be designed such that they add facilitate additional engagement with surrounding tissue. It is understood that a variety of shapes and sizes could be used, and the features could be located anywhere along the lead ribbon.

Figure 4A:
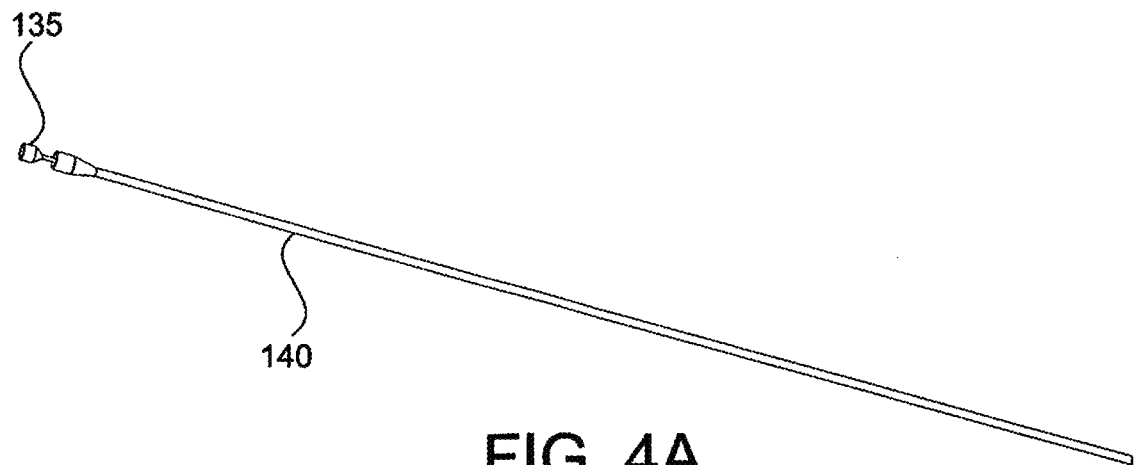
FIGS. 4A, 4B, and 4C depict perspective views of an exemplary lead ribbon installed in a needle with a stylet.
Figure 4B:
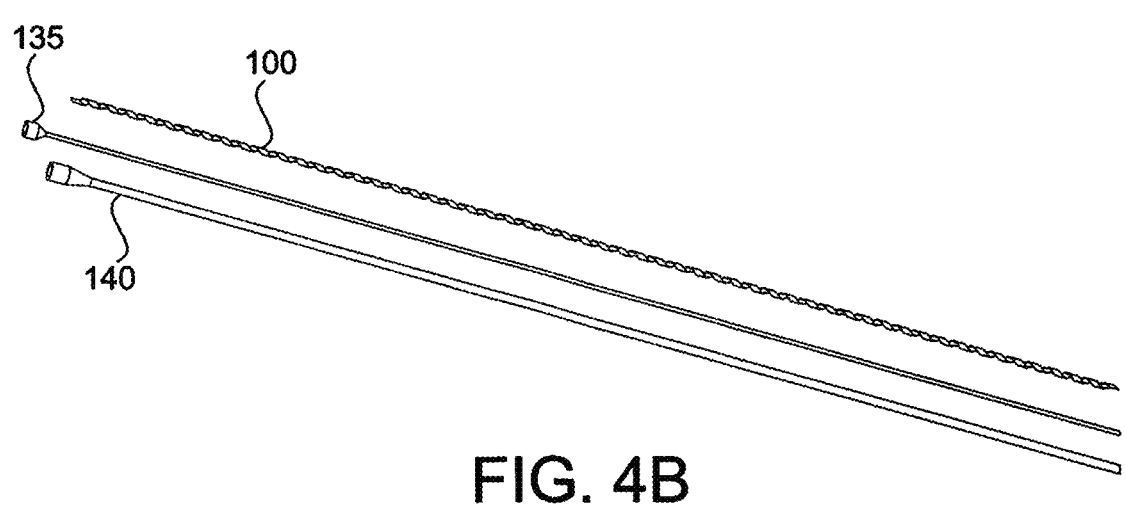
Figure 4C:
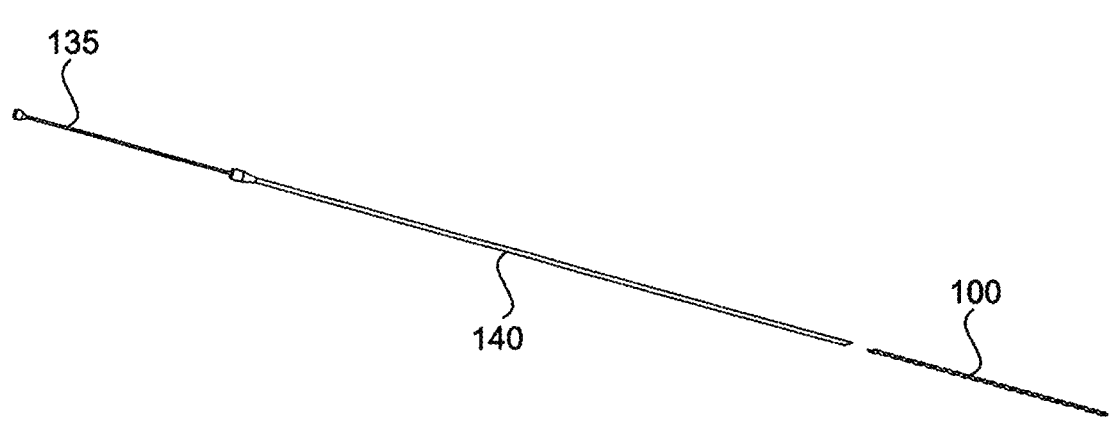

FIGS. 4A, 4B, and 4C depict perspective views of an exemplary lead ribbon installed in a needle with a stylet. A stylet 135 is inserted in a (hollow) needle 140, with a lead ribbon 100 residing inside of the needle 140. The lead ribbon is installed in the needle with the stylet.

Figure 5A:
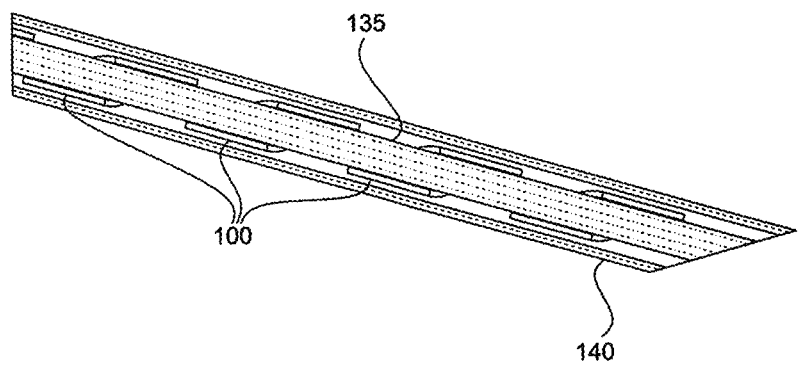
FIGS. 5A and 5B depict cross-sectional views (longitudinal and lateral cross sections) of an exemplary needle, stylet, and lead assembly.
Figure 5B:
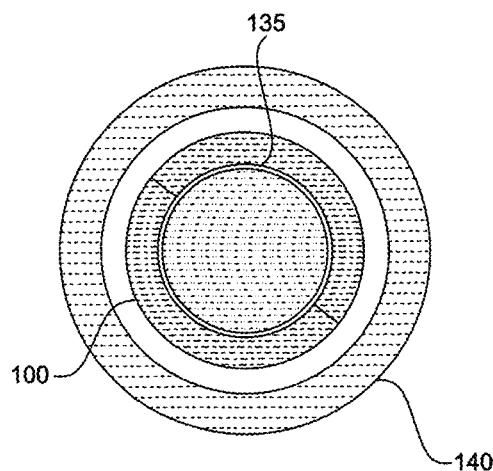

FIGS. 5A and 5B depict cross-sectional views (longitudinal and lateral cross sections) of an exemplary needle, stylet, and lead assembly. The longitudinal and lateral cross section of the assembly reveals the lead ribbon 100 wrapped around the stylet 135 within the needle 140, prepared for insertion into the patient.

Figure 6:
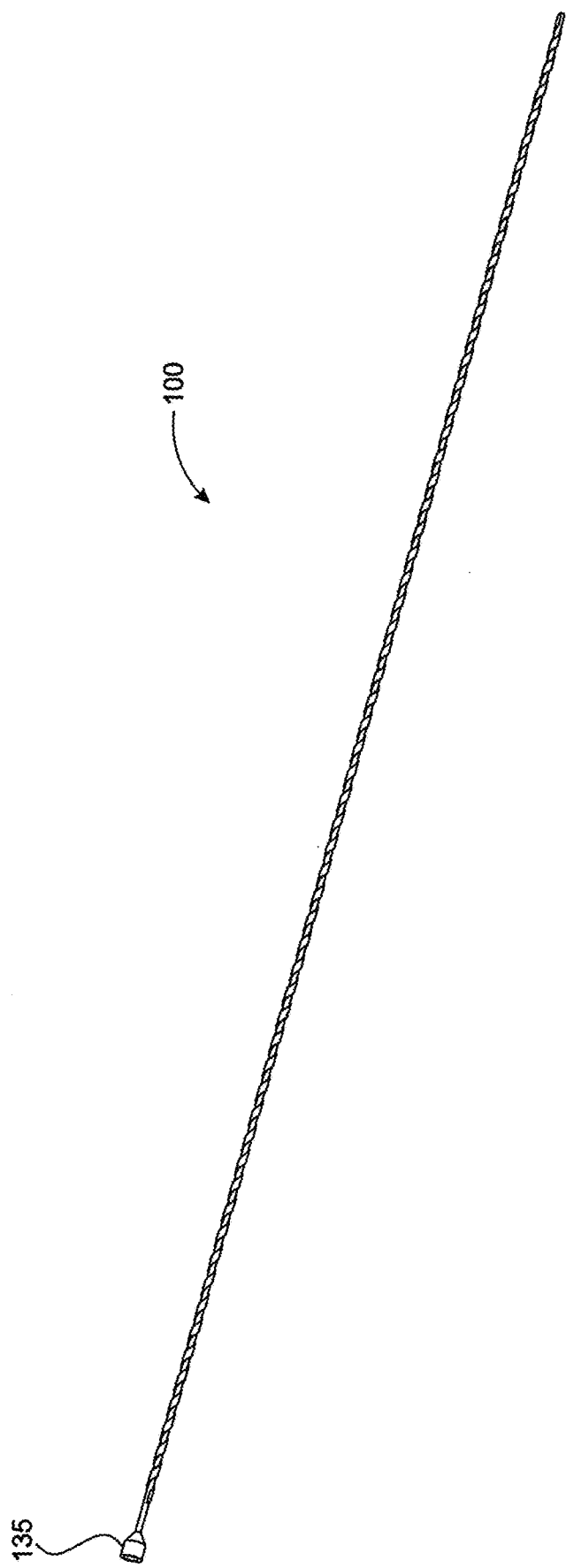
FIG. 6 depicts a perspective view of an exemplary ribbon lead wrapped around an exemplary stylet.

FIG. 6 depicts a perspective view of an exemplary ribbon lead wrapped around an exemplary stylet. After insertion into a patient near the stimulation target, the needle 140 may be withdrawn, as shown in FIG. 6.

Figure 7:
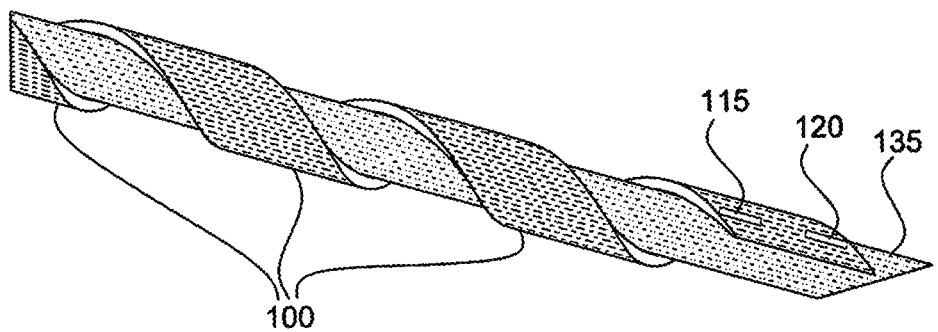
FIG. 7 depicts a perspective view of a distal end of an exemplary lead and stylet assembly.

FIG. 7 depicts a perspective view of a distal end of an exemplary lead and stylet assembly. This illustration shows a detailed view with the needle removed (traces and fixation features are not shown for clarity). In some examples, the stylet may advance to push the lead out of the tip, which may allow the lead to spring open and catch the surrounding tissue. Then the stylet may be slid out, and then the needle slid out over the lead.

Figure 8:
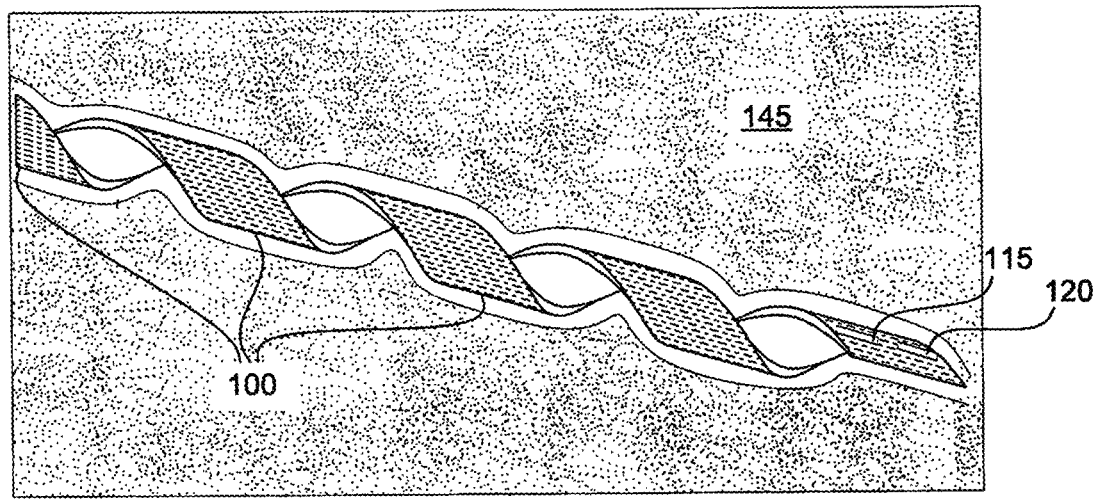
FIG. 8 depicts a perspective view of an exemplary lead embedded inside tissue.

FIG. 8 depicts a perspective view of an exemplary lead embedded inside tissue. Once the needle is removed, and the stylet withdrawn, the spiral wound ribbon 100 will tend to expand radially, engaging the tissue as shown in FIG. 8. The (optional) fixation members/features (not shown) may provide additional engagement with the surrounding tissue. The spiral form of the ribbon may allow some stretch of the lead as the patient moves, minimizing the chance of dislodgement. When it is time to remove the lead, the proximal end of the ribbon can be grasped and pulled. This may cause the ribbon to unwind and easily come out of the patient.

Figure 9:
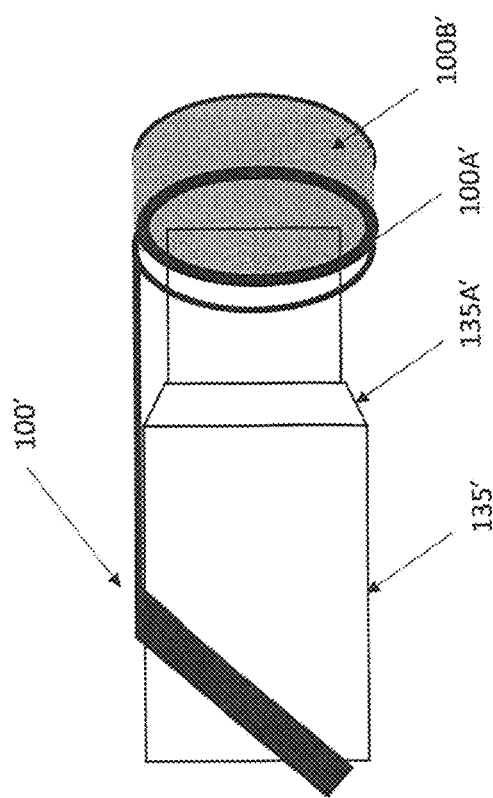
FIG. 9 depicts a side elevation view of an exemplary ribbon wrapped around a stepped stylet to form an inner wrap and an outer wrap.

FIG. 9 depicts a side elevation view of an exemplary ribbon wrapped around a stepped stylet to form an inner wrap and an outer wrap. As seen in FIG. 9, a ribbon 100' is featured that is wrapped more than 360 degrees around a stylet 135'. The stylet 135' includes an area providing a step or shoulder 135A' for the stylet 135 to push against the ribbon 100'. The ribbon 100' is wrapped greater than 360 degrees, such that the ribbon 100' forms an inner ribbon wrap 100A' and an outer ribbon wrap 100B'. The step/shoulder 135' on the stylet 135' engages a step formed between the inner and outer wraps 100A', 100B', which advantageously aids in pushing the ribbon 100' out of the tube (not shown).

Although various embodiments have been described with reference to the Figures, other embodiments are possible. In various examples, a lead for temporary stimulation of a peripheral nerve includes a lead ribbon. The lead ribbon may include a lead ribbon substrate. The lead ribbon may include at least one trace running along a length of the lead ribbon substrate between a lead ribbon proximal end to a lead ribbon distal end. The lead ribbon may include a pair of electrodes located at the lead ribbon distal end and in electrical communication with the at least one trace, respectively. The lead ribbon may include at least one exposed electrical stimulation pad located at the lead ribbon proximal end and in electrical communication with the at least one trace. The lead for temporary stimulation of a peripheral nerve may include a stylet. The lead ribbon may be wrapped around the stylet such that an exposed surface of the at least one electrical stimulation pad is oriented radially outward relative to the stylet.

The lead for temporary stimulation of a peripheral nerve may include a hollow needle in which the lead ribbon wrapped around the stylet resides. The at least one trace may be enclosed by electrical insulation, the electrical insulation extending between the lead ribbon proximal end to the lead ribbon distal end. The lead ribbon may be helically wrapped around the stylet. The lead ribbon may include multiple fixation features disposed along the length of the lead ribbon and configured to fixingly engage with surrounding patient tissue. The multiple fixation features include a plurality of teeth located on opposing lateral sides of the lead ribbon. The lead ribbon may include a springing lead ribbon configured to spring open and catch surrounding patient tissue after the lead ribbon is released from the stylet inside a patient. After the lead ribbon is released from the stylet inside the patient, the lead ribbon may be configured to expand radially to retainingly engaging surrounding patient tissue. The lead ribbon may be stretchable along a longitudinal axis defined by the stylet. In some embodiments, the at least one trace may include a pair of traces, the at least one electrode trace may include a pair of electrode, and the at least one exposed electrical stimulation pad trace may include a pair of exposed electrical stimulation pads, the pair of electrodes may be in electrical communication with the pair of traces, respectively, and the pair of exposed electrical stimulation pads may be in electrical communication with the pair of traces, respectively. In some embodiments, the stylet may include a stepped stylet. In some embodiments, the lead ribbon may be configured to wrap around the stylet more than 360 degrees to form an inner ribbon wrap and an outer ribbon wrap.

A method for the insertion of a lead for temporary stimulation of a peripheral nerve may include inserting into an electrical stimulation assembly into a patient proximate to a stimulation target. The electrical stimulation assembly may include a lead ribbon. The lead ribbon may include a lead ribbon substrate, at least one trace running along a length of the lead ribbon substrate between a lead ribbon proximal end to a lead ribbon distal end, at least one electrode disposed at the lead ribbon distal end and in electrical communication with the at least one trace, respectively, and at least one exposed electrical stimulation pads disposed at the lead ribbon proximal end and in electrical communication with the at least one trace, respectively. The electrical stimulation assembly may include a stylet, where the lead ribbon may be helically wrapped around the stylet such that an exposed surface of the at least one electrical stimulation pad is oriented radially outward relative to the stylet. The electrical stimulation assembly may include a hollow needle in which the lead ribbon wrapped around the stylet resides. The method may include advancing the stylet to push the stylet out of a tip of the hollow needle to effectuate springing open of the lead ribbon to catch surrounding tissue. The method may include sliding the stylet out from the surrounding tissue and separating the stylet from the lead ribbon and hollow needle. The method may include sliding the hollow needle out from the surrounding tissue and separating the hollow needle from the lead ribbon. The method may include expanding the helically oriented lead ribbon radially outward to engage the surrounding tissue.

In some embodiments, the at least one trace may include a pair of traces, the at least one electrode may include a pair of electrodes, and the at least one exposed electrical stimulation pad may include a pair of exposed electrical stimulation pads, the pair of electrodes may be in electrical communication with the pair of traces, respectively, and the pair of exposed electrical stimulation pads may be in electrical communication with the pair of traces, respectively. In various implementations, the proximal pads may not be exposed, with connection made via an insulation displacement connector. In such an implementation there would not even need to be a specific pad (per se), and connection could be made to the trace. In such implementations, the lead could be cut off to be made shorter, if so desired.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are within the scope of the following claims.

What is claimed is:

1. A lead for temporary stimulation of a peripheral nerve, the lead comprising:
   a lead ribbon comprising:
      a substantially flat lead ribbon substrate extending substantially in a first plane when in an unwound state;
      at least one trace running along a length of the lead ribbon substrate between a lead ribbon proximal end to a lead ribbon distal end;
      at least one electrode disposed at the lead ribbon distal end and in electrical communication with the at least one trace;
      at least one exposed electrical stimulation pad disposed at the lead ribbon proximal end and in electrical communication with the at least one trace; and,
      a plurality of fixation features extending in the first plane form at least a first edge of the lead ribbon substrate when the lead ribbon substrate is in the unwound state; and,
   a stylet, wherein the lead ribbon is wrapped around the stylet such that an exposed surface of the at least one electrical stimulation pad is oriented radially outward relative to the stylet,
   wherein, when the lead ribbon is deployed from the stylet within a lumen in tissue such that the plurality of fixation features engage the tissue and the lead ribbon proximal end is pulled, then the lead ribbon unwinds such that the plurality of fixation features disengage from the tissue.

2. The lead of claim 1, further comprising a hollow needle in which the lead ribbon wrapped around the stylet resides.

3. The lead of claim 1, wherein the at least one trace is enclosed by electrical insulation, the electrical insulation extending between the lead ribbon proximal end to the lead ribbon distal end.

4. The lead of claim 1, wherein the at least one trace comprises a pair of traces, the at least one electrode comprises a pair of electrodes, and the at least one exposed electrical stimulation pad comprises a pair of exposed electrical stimulation pads, and the pair of electrodes are in electrical communication with the pair of traces, respectively, and the pair of exposed electrical stimulation pads are in electrical communication with the pair of traces, respectively.

5. The lead of claim 1, wherein the lead ribbon is helically wrapped around the stylet.

6. The lead of claim 1, wherein the plurality of fixation features comprise a plurality of teeth disposed on opposing lateral sides of the lead ribbon.

7. The lead of claim 1, wherein the lead ribbon comprises a springing lead ribbon configured to spring open and catch surrounding patient tissue after the lead ribbon is released from the stylet inside a patient.

8. The lead of claim 7, wherein after the lead ribbon is released from the stylet inside the patient, the lead ribbon is configured to expand radially to retainingly engaging surrounding patient tissue.

9. The lead of claim 7, wherein the lead ribbon is stretchable along a longitudinal axis defined by the stylet.

10. The lead of claim 1, wherein the stylet comprises a stepped stylet.

11. The lead of claim 1, wherein the lead ribbon is configured to wrap around the stylet more than 360 degrees to form an inner ribbon wrap and an outer ribbon wrap.

12. A method for insertion of a lead for temporary stimulation of a peripheral nerve, the method comprising:
   inserting into an electrical stimulation assembly into a patient proximate to a stimulation target, wherein the electrical stimulation assembly comprises:
      a lead ribbon comprising:
         a substantially flat lead ribbon substrate extending in a first plane when in an unwound state;
         at least one trace running along a length of the lead ribbon substrate between a lead ribbon proximal end to a lead ribbon distal end;
         at least one electrode disposed at the lead ribbon distal end and in electrical communication with the at least one trace;
         at least one exposed electrical stimulation pad disposed at the lead ribbon proximal end and in electrical communication with the at least one trace; and,
         a plurality of fixation members extending in the first plane form at least a first edge of the lead ribbon substrate when the lead ribbon substrate is in the unwound state; and,
      a stylet, wherein the lead ribbon is wrapped around the stylet such that an exposed surface of at least one electrical stimulation pad is oriented radially outward relative to the stylet; and,
      a hollow needle in which the lead ribbon wrapped around the stylet resides;
   advancing the stylet to push the stylet out of a tip of the hollow needle to effectuate springing open of the lead ribbon to catch surrounding tissue,
   sliding the stylet out from the surrounding tissue and separating the stylet from the lead ribbon and hollow needle,
   sliding the hollow needle out from the surrounding tissue and separating the hollow needle from the lead ribbon,
   expanding the lead ribbon radially outward such that the plurality of fixation members engage the surrounding tissue, and, pulling the lead ribbon proximal end to unwind the lead ribbon such that the plurality of fixation members disengage from the tissue.

13. The method of claim 12, wherein the at least one trace comprises a pair of traces, the at least one electrode comprises a pair of electrodes, and the at least one exposed electrical stimulation pad comprises a pair of exposed electrical stimulation pads, and the pair of electrodes are in electrical communication with the pair of traces, respectively, and the pair of exposed electrical stimulation pads are in electrical communication with the pair of traces, respectively.

14. The method of claim 13, wherein the pair of traces are enclosed by electrical insulation, the electrical insulation extending between the lead ribbon proximal end to the lead ribbon distal end.

15. The method of claim 12, wherein the lead ribbon comprises a springing lead ribbon configured to spring open and catch surrounding patient tissue after the lead ribbon is released from the stylet inside a patient.

16. The method of claim 12, wherein after the lead ribbon is released from the stylet inside the patient, the lead ribbon is configured to expand radially to retainingly engaging surrounding patient tissue.

17. The method of claim 12, wherein the lead ribbon is stretchable along a longitudinal axis defined by the stylet.

18. The method of claim 12, wherein the lead ribbon is helically oriented when wrapped around the stylet.

19. A lead for temporary stimulation of a peripheral nerve, the lead comprising:
   a lead ribbon comprising:
      a substantially flat lead ribbon substrate extending in a first plane when in an unwound state;
      a pair of traces running along a length of the lead ribbon substrate between a lead ribbon proximal end to a lead ribbon distal end;
      a pair of electrodes disposed at the lead ribbon distal end and in electrical communication with the pair of traces, respectively; and,
      a pair of exposed electrical stimulation pads disposed at the lead ribbon proximal end and in electrical communication with the pair of traces, respectively;
   a stylet, wherein the lead ribbon is wrapped around the stylet such that an exposed surface of each of the pair of electrical stimulation pads are oriented radially outward relative to the stylet; and,
   a plurality of means for fixation extending in the first plane from at least a first edge of the lead ribbon substrate when the lead ribbon substrate is in the unwound state and disposed along the length of the lead ribbon and configured to fixingly engage with surrounding patient tissue, the plurality of means for fixation further configured to disengage from the tissue when the lead ribbon proximal end is pulled.

20. The lead of claim 19, the lead ribbon further configured such that, when the lead ribbon proximal end is pulled, the lead ribbon unwinds such that the plurality of means for fixation disengage from the tissue.

* * * * *